(12) United States Patent
Donohue

(10) Patent No.: US 6,997,184 B2
(45) Date of Patent: Feb. 14, 2006

(54) COOL AIR INHALER

(76) Inventor: Timothy J. Donohue, 55 Cedar St., Apartment 2350, Woburn, MA (US) 01810

( * ) Notice: Subject to any disclaimer, the term of this patent is extended or adjusted under 35 U.S.C. 154(b) by 0 days.

(21) Appl. No.: 10/827,410

(22) Filed: Apr. 19, 2004

(65) Prior Publication Data
US 2005/0229930 A1 Oct. 20, 2005

(51) Int. Cl.
A61M 16/00 (2006.01)
A61M 15/08 (2006.01)
A62B 7/00 (2006.01)
A62B 9/02 (2006.01)
F24F 5/00 (2006.01)

(52) U.S. Cl. .......................... 128/204.15; 128/204.14; 128/204.16; 128/205.24; 128/203.24; 128/200.11; 128/200.14; 128/200.24; 128/203.12; 128/203.16; 128/203.26; 128/203.29; 62/420; 62/424

(58) Field of Classification Search .......... 128/204.15, 128/200.11, 200.14, 200.24, 203.12, 203.16, 128/203.26, 203.29, 204.14, 204.16, 203.24, 128/205.24; 62/420, 424
See application file for complete search history.

(56) References Cited

U.S. PATENT DOCUMENTS

| 3,140,590 | A | * | 7/1964 | Gleockler | 62/259.3 |
|---|---|---|---|---|---|
| 5,146,757 | A | * | 9/1992 | Dearing | 62/61 |
| 5,605,146 | A | * | 2/1997 | Sarela | 128/203.12 |
| 5,630,409 | A | * | 5/1997 | Bono et al. | 128/200.18 |
| 5,655,520 | A | * | 8/1997 | Howe et al. | 128/203.12 |
| 5,906,198 | A | * | 5/1999 | Flickinger | 128/200.21 |
| 6,138,672 | A | * | 10/2000 | Kankkunen | 128/203.12 |
| 6,170,282 | B1 | * | 1/2001 | Eddins | 62/259.3 |
| 6,530,374 | B1 | * | 3/2003 | Ferraro | 128/206.29 |
| 6,568,202 | B1 | * | 5/2003 | Hodges | 62/306 |
| 6,571,574 | B1 | * | 6/2003 | Blackstone | 62/420 |
| 6,901,769 | B1 | * | 6/2005 | Blackstone | 62/420 |

* cited by examiner

Primary Examiner—Henry Bennett
Assistant Examiner—Nihir Patel
(74) Attorney, Agent, or Firm—Davis & Bujold, P.L.L.C.

(57) ABSTRACT

A cool air inhaler for use in treating croup, having a body having at least one side wall and a bottom wall forming an enclosed space open at an upper portion of the body wherein the upper portion of the body is adapted to generally conform to contours of a lower part of a patient face. An air chamber is formed in an upper part of the body and has an exhaust vent for exhausting the patient's exhaled air to an exterior space while an ice reservoir is formed in a lower part of the body to contain ice and meltwater from the ice and an air passage is connected from the exterior space and passing through the ice reservoir to conduct air to the air chamber.

3 Claims, 1 Drawing Sheet

COOL AIR INHALER

FIELD OF THE INVENTION

The present invention relates to a medical inhalation device for relief fro symptoms of respiratory illnesses and, in particular, to a cool air inhaler for treatment of croup by non-medical personnel, including a patient.

BACKGROUND OF THE INVENTION

There are a number of diseases and conditions that may cause upper respiratory tract symptoms that, while they may not rise to a ciritical condition, may result in notable discomfort, such as severe coughing, that can result, for example, in exhaustion, severe loss of sleep or rest, inability to concentrate on tasks, and so on.

One of the most common of such diseases is "croup", which is a viral infection of the upper and lower airways that can be caused by a range of viruses and that causes difficulty in breathing, especially when inhaling. The symptoms of croup may initially be similar to those of the common cold, but croup will cause swelling of the lining of the airway, causing the airway to narrow and making breathing difficult, resulting in, for example, a barking cough and hoarseness.

Croup may also appear in repeated episodes for various reasons, including allergies.

Certain croup symptoms, such as coughing, result from the narrowing and drying of the upper airway and relief for croup symptoms, at least in milder cases, may be obtained by providing the patient with cool and preferably moist air to breath.

The traditional ways of treating the symptoms of croup include humidifiers, cool mist vaporizers or ultrasonic nebulizers, providing warm, moist air, such as in a shower, and taking the patient into an environment having cooler and preferably moist air, such as taking the patient outside in suitably cool weather. All of these methods, however, suffer from the same disadvantage of being cumbersome and inconvenient to use. For example, humidifiers, cool mist vaporizers or ultrasonic nebulizers require confining the patient to a relatively small area, as does the use of a hot shower, which confines the patient to a space that is relatively smaller and that can be very uncomfortable. In a like manner, going outdoors into cooler and perhaps moister air is useful only if the air outside is in fact cooler and moister; this method may not be practical in, for example, Arizona in the summer. It will also be appreciated that these problems are compounded when the symptoms are relatively mild, so that the patient is not completely exhausted, and when, for example, the patient is an active child.

The present invention offers solutions to these and related problems.

SUMMARY OF THE INVENTION

The present invention is directed to a cool air inhaler for use in treating croup. The inhaler includes a body having at least one side wall and a bottom wall forming an enclosed space open at an upper portion of the body wherein the upper portion of the body is adapted to generally conform to contours of a lower part of a patient face. An air chamber is formed in an upper part of the body and has an exhaust vent for exhausting the patient's exhaled air to an exterior space while an ice reservoir is formed in a lower part of the body to contain ice and meltwater from the ice and an air passage is connected from the exterior space and passing through the ice reservoir to conduct air to the air chamber.

According to the present invention, intake air is drawn from the exterior and through the air passage into the chamber when the patient inhales air from the chamber such that the intake air in the air chamber is cooled and moistened by the ice in the ice reservoir so that the patient can thereby inhale cool, moistened air from the air chamber. The exhaust air exhaled by the patient is in turn vented from the air chamber through the exhaust vent.

Further according to the present invention, the air passage further includes a one way intake valve that is preferably formed as a self-hinged membrane of resilient material and the exhaust valve is a self-hinged membrane of resilient material.

Also, the air passage includes an air intake tube having an intake opening in the bottom wall of the body and having an output above the ice reservoir and into the air chamber through the intake valve.

BRIEF DESCRIPTION OF THE DRAWING(S)

The invention will now be described, by way of example, with reference to the accompanying drawings in which.

DETAILED DESCRIPTION OF THE INVENTION

Figure 1:
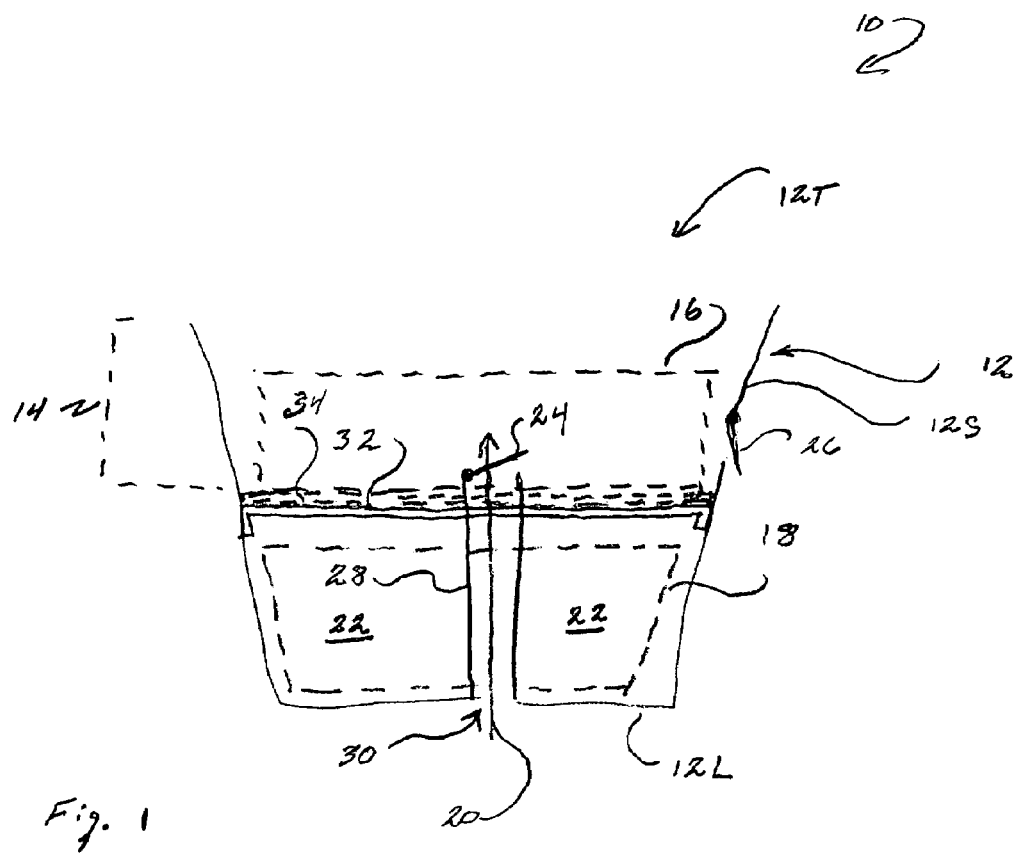
FIG. 1 is a diagrammatic cross section of a cool air inhaler.

Referring to FIG. 1, therein is shown a diagrammatic cross section view of a Cool Air Inhaler (Inhaler) 10 of the present invention. As illustrated therein, a Inhaler 10 includes a generally cup-shaped Body 12 having a generally cylinderical Side Wall 12S, a Lower Wall 12L closing off the bottom of Side Wall 12S, and an open Top 12T, thereby forming an enclosed space having an open top. As indicated, the upper portion of Body 12 forms having a Mask 14 portion wherein open Top 12T generally fits over a patient's mouth and nose. For this purpose, the upper portion of Body 12 is either shaped to the average general lower face contours of a patient or is sufficiently resiliently deformable to generally conform to the lower face contours of a patient under relatively low force.

In this regard, it should be noted that the confomity of Mask 14 to a patient's lower facial contours need only be approximate as Inhaler 10 is not delivering valuable or rare gases or medicated gases to the patient. Leaks in the fit of Mask 14 to the patient's lower face are thereby acceptable unless they rise to a level that essentially prevents the delivery of cool, moist air to the patient. In fact, it may be preferable to not have a close fit between Mask 14 and the patient's face as Inhaler 10 is intended for use by a patient, who may be a child, without assistance if need be and without close supervision, and in particular without the need for medical supervision, as on over-the-counter type device. As an Inhaler 10 is intended to be an over-the-counter, inexpensive and readily disposable device, an Inhaler 10 may be molded from a rubber-like or plastic type material, or may be molded of styrefoam, for example.

As illustrated, when Mask 14 is fitted to a patient's lower face, the Mask 14 and the patient's lower face together form a Cool Air Chamber (Chamber) 16 from which the patient draws cool, moist air when breathing through the Inhaler 10. The lower portion of Body 12 is in turn formed to include an Ice Reservoir (Reservoir) 18 and an Air Path 20 forming an air flow path from the exterior air and over or through Ice 22 residing in Reservoir 18 and to Chamber 16 to be breathed by the patient, so that the air flowing to the patient is thereby chilled by Ice 22 and picks up moisture from Ice 22. While Air Path 20 may begin at any lower surface of Body 12, such as in Lower Wall 12L, Air Path 20 is preferably formed to allow the maximum length of air flow path over or through Ice 22.

In use, therefore, the patient inhales cool, moist air from Chamber 16 and exterior air flows into the Body 12 through Air Path 20 and a one-way Intake Valve 24 located in Air Path 20 and over or through Ice 22, there becoming chilled and moistened. The cool, moist air then from from Air Path 20 and into Chamber 16 to replace the cool, moist air inhaled by the patient. Air exhaled by the patient, in turn, enters Chamber 16 and is vented from Chamber 16 and Mask 14 and to the exterior through a one-way Exhaust Vent (Vent) 26 when the patient exhales.

Considering the design of the elements of a Inhaler 10 in further detail, it must be noted that Reservoir 18 must not only securely contain Ice 22 but must also capture and hold meltwater from Ice 22. This requirement, in turn, effects the dimensions and may effect the shape of Reservoir 18. For example, the size and depth of Reservoir 18 must be sufficient to accomodate both a reasonable supply of Ice 22 and the resulting meltwater, and Air Path 20 and Intake Valve 24 must be designed to prevent leaks and spills out through Air Path 20 and to prevent the blocking or flooding of Air Path 20 or Intake Valve 24 by Ice 22 or the meltwater.

In addition, the length and configuration of Air Path 20 must be such as to provide sufficient cooling and moistening of the air provided to the patient from Chamber 16. In a presently preferred embodiment, for example, the contact and circulation between the air and the top surface or surfaces of Ice 22 in Reservoir 18 has been found satisfactory to adequately cool and moisturize the air. In other implementations, however, Air Path 20 may be configured to increase the path length and time of contact between the air and Ice 22.

In a typical and presently preferred embodiment, for example, Air Path 20 is formed by an Intake Tube 28 extending generally vertically upwards from an Intake Opening 30 located in Lower Wall 12L for a distance sufficient to bring the top of Intake Tube 28 to or above the top level of Ice 22. The topmost end of Intake Tube 28 thereby vents the intake air directly into Chamber 16, where the natural circulation of air in Chamber 16 will bring the air into contact with Ice 22 so that the air is cooled and moisturized.

In this embodiment, and as illustrated, Intake Valve 24 is located at the topmost end of Intake Tube 28, and is thereby above the topmost level of Ice 22 and meltwater from Ice 22, and is preferably and for example a simple flap valve, such as a self-hinged membrane of resilient material, such as a plastic or a rubber-like material. Other possibilities include, for example, a resiliently self-closing tube, similar to the mouthpiece of a balloon. It should also be noted that Vent 26 may be implemented in a similar manner, and is preferably implemented as a simple flap valve, such as a self-hinged membrane of resilient material.

Figure 2A:
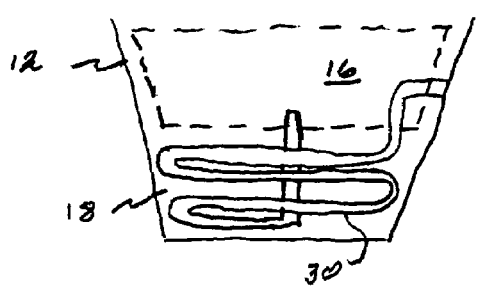
FIGS. 2A and 2B are diagrammatic illustrations of implementations of the inhaler air passage.
Figure 2B:
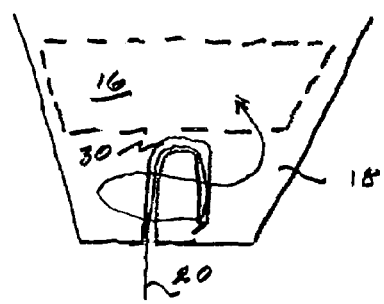

In other implementations, such as illustrated in FIGS. 2A and 2B. Intake Tube 28 may start at an Intake Opening 30, which may, for example, be located in Lower Wall 12L or in a Side Wall 12S and which may follow any extended path through or around within Reservoir 18.to finally exit in Chamber 16, thereby providing greater opportunity for the air to become chilled while passing through Air Path 20 and before coming into contact with Ice 22 in the lower portion of Chamber 16.

In yet another implementation, Intake Tube 28 may start in the side or bottom wall of body 12, as described above, but may vent within Reservoir 18 below the top of Ice 22, and perhaps below the highest level the meltwater is expected to reach, thereby forcing the intake air to pass through Ice 22 before reaching Chamber 16. In this instance, the vent end of Intake Tube 28 may be formed into an inverted U, thereby forming a "snorkel" configuration and prevent Ice 22 and the meltwater from entering Intake Tube 28.

In yet further implementations, and for example, Chamber 16 may be separated from Reservoir 18 by a Barrier 32, which may be a panel or membrane extending across the interior of Body 12 above Reservoir 18 and held in position, for example, by a friction fit rim. Barrier 32 may be formed, for example, of a mesh or a panel with suitable openings therethrough and one of the functions of a Barrier 32 is to assist in retaining Ice 22 in Reservoir 18. Barrier 32 may also be an element of Air Path 20 in that Intake Tube 28 may terminate at or above Barrier 32 with Barrier 32 acting as a support for Intake Tube 28. Intake Tube 28 may also terminate below Barrier 32 to retain the intake air in contact with Ice 22 in the space between Barrier 32 and Ice 22 for a longer period, that is, until the intake air filters into Chamber 16 through the mesh or openings of Barrier 32, thereby further cooling and moisturizing the air.

It should also be noted that Barrier 32 will also function as a retainer to retain Ice 22 in Reservoir 18 and will thereby prevent or reduce the changes of ingestion or inhalation of Ice 22 from Reservoir 18 by a user of the Inhaler 10, particularly in the case of a child user and in particular when Ice 22 is crushed ice. In certain embodiments, this function may be performed by a separate Retainer 34 which would be generally similar to Barrier 32 but may, for example, be formed from a mesh while Barrier 32 is more specifically formed to to function as a part of Air Path 20 to, for example, slow the passage of air through Reservoir 18.

Lastly, in typical embodiments it is intended that Reservoir 18 may be filled with Ice 22 in any convenient form, such as ice cubes or crushed ice. In certain implementations, Reservoir 18 may be filled with water and placed in a freezer before use to form a single block of Ice 22 filling at least part of Reservoir 18.

Since certain changes may be made in the above described invention without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, I claim:

1. A cool air inhaler, comprising:
   a body having at least one side wall and a bottom wall forming an enclosed space open at an upper portion of the body,
   the upper portion of the body being adapted to generally conform to contours of a lower part of a patient face,
   an air chamber formed In an upper part of the body and having an exhaust vent for exhausting the patient's exhaled air to an exterior space,
   an ice reservoir formed in a lower part of the body to contain ice and meltwater from the ice, and an air passage connected from the exterior space and passing through the ice reservoir to conduct air to the air chamber, wherein intake air is drawn from the exterior space and through the air passage into the chamber when the patient inhales air from the chamber such that the intake air in the air chamber is cooled and moistened by the ice in the ice reservoir, so that the patient Inhales cool, moistened air from the air chamber, and exhaust air exhaled by the patient is vented from the air chamber through the exhaust vent, wherein the air passage includes an air intake tube having an intake opening in the bottom wall of the body and having an output above the ice reservoir and into the air chamber through the intake valve.

2. A cool air inhaler, comprising:

a body having at least one side wall and a bottom wall forming an enclosed space open at an upper portion of the body, the upper portion of the body being adapted to generally conform to contours of a lower part of a patient face, an air chamber formed in an upper part of the body and having an exhaust vent for exhausting the patient's exhaled air to an exterior space, an ice reservoir formed in a lower part of the body to contain ice and meltwater from the ice, and an air passage connected from the exterior space and passing through the ice reservoir to conduct air to the air chamber, wherein intake air is drawn from the exterior space and through the air passage into the chamber when the patient inhales air from the chamber such that the intake air in the air chamber is cooled and moistened by the ice in the ice reservoir, so that the patient inhales cool, moistened air from the air chamber, and exhaust air exhaled by the patient is vented from the air chamber through the exhaust vent, wherein the air passage includes an air intake tube having an Intake opening in the bottom wall of the body and having an output above a meltwater level in the ice reservoir to allow the passage of intake air into the air chamber.

3. A cool air inhaler, comprising:

a body having at least one side wall and a bottom wall forming an enclosed space open at an upper portion of the body, the upper portion of the body being adapted to generally conform to contours of a lower part of a patient face, an air chamber formed in an upper part of the body and having an exhaust vent for exhausting the patient's exhaled air to an exterior space, an ice reservoir formed in a lower part of the body to contain ice and meltwater from the ice, and an air passage connected from the exterior space and passing through the ice reservoir to conduct air to the air chamber, wherein intake air is drawn from the exterior space and through the air passage into the chamber when the patient inhales air from the chamber such that the intake air in the air chamber is cooled and moistened by the ice in the ice reservoir, so that the patient inhales cool, moistened air from the air chamber, and exhaust air exhaled by the patient is vented from the air chamber through the exhaust vent, wherein the air passage includes an air intake tube having an intake operating in the bottom wall of the body and having an upper portion formed into an inverted U-shape within the ice reservoir with a terminal opening located in the ice reservoir to allow the passage of intake air into the air chamber.

* * * * *